(12) United States Patent  
Barak

(10) Patent No.: US 9,314,607 B2
(45) Date of Patent: Apr. 19, 2016

(54) VENTED LUER TIP CONNECTOR

(71) Applicant: Swi Barak, Caesarea (IL)

(72) Inventor: Swi Barak, Caesarea (IL)

(*) Notice: Subject to any disclaimer, the term of this patent is extended or adjusted under 35 U.S.C. 154(b) by 285 days.

(21) Appl. No.: 13/847,663

(22) Filed: Mar. 20, 2013

(65) Prior Publication Data

US 2014/0288510 A1    Sep. 25, 2014

(51) Int. Cl.
*A61M 39/12* (2006.01)
*A61M 5/34* (2006.01)
*A61M 5/31* (2006.01)
*A61M 39/10* (2006.01)
*A61M 5/14* (2006.01)
*A61M 5/162* (2006.01)
*A61J 1/16* (2006.01)

(52) U.S. Cl.
CPC .............. *A61M 39/12* (2013.01); *A61M 5/1417* (2013.01); *A61M 5/162* (2013.01); *A61M 5/3134* (2013.01); *A61M 5/345* (2013.01); *A61M 39/10* (2013.01); *A61J 1/16* (2013.01); *A61J 1/2068* (2015.05); *A61M 2005/1623* (2013.01)

(58) Field of Classification Search
CPC .............. A61J 1/16; A61J 2001/2068; A61M 2005/1623; A61M 39/12; A61M 5/1417; A61M 5/162; A61M 5/3134; A61M 5/345; A61M 39/00; A61M 39/10; A61M 2039/1077
See application file for complete search history.

(56) References Cited

U.S. PATENT DOCUMENTS

| | | | | |
|---|---|---|---|---|
| 3,631,654 A * | 1/1972 | Riely | .................... | A61M 5/165 210/446 |
| 3,833,030 A * | 9/1974 | Waldbauer, Jr. | .... | A61M 5/1782 141/26 |
| 4,588,403 A * | 5/1986 | Weiss et al. | ................... | 604/411 |
| 4,657,486 A * | 4/1987 | Stempfle | ............... | A61M 5/142 417/12 |
| 4,787,898 A * | 11/1988 | Raines | ................... | A61M 5/162 604/126 |
| 4,899,877 A * | 2/1990 | Kiernan | ............... | B65D 75/245 206/349 |
| 4,979,616 A * | 12/1990 | Clanton | .............. | A61M 5/3205 206/364 |
| 5,156,267 A * | 10/1992 | Yates et al. | ..................... | 206/364 |
| 5,209,354 A * | 5/1993 | Thornhill | ............. | B65D 43/163 206/461 |
| 5,441,487 A * | 8/1995 | Vedder | ................ | A61M 39/045 604/167.03 |
| 5,674,200 A * | 10/1997 | Ruschke | .................. | A61M 5/38 604/122 |
| 5,855,230 A * | 1/1999 | Guala | .................... | A61M 39/20 138/89 |
| 5,873,859 A * | 2/1999 | Muntz | .................... | A61J 1/2096 141/27 |
| 5,911,710 A * | 6/1999 | Barry | ................ | A61M 39/0693 604/167.04 |
| 6,364,866 B1 * | 4/2002 | Furr et al. | ..................... | 604/414 |
| 6,439,276 B1 * | 8/2002 | Wood | .................. | A61M 5/1782 141/27 |
| 6,511,472 B1 * | 1/2003 | Hayman | ........... | A61M 25/0097 604/533 |
| 6,669,673 B2 * | 12/2003 | Lopez | ..................... | A61M 5/14 604/247 |
| 6,706,022 B1 | 3/2004 | Leinsing et al. | | |
| 7,184,825 B2 | 2/2007 | Leinsing et al. | | |
| 7,431,712 B2 * | 10/2008 | Kim | ........................ | A61M 5/36 604/256 |

(Continued)

*Primary Examiner* — Quynh-Nhu H Vu
(74) *Attorney, Agent, or Firm* — Mark David Torche; Patwrite LLC

(57) ABSTRACT

A vented connector, used with male Luer tip fitting, is disclosed. The connector includes axial and bifurcating portions. The axial portion includes an exterior housing and interior post. The lumen of the post forms a continuum with an air inlet. The air inlet is furnished with a filter or membrane element, selectively allowing for the flow of air to pass therethrough while preventing an outflow of fluids therefrom. The outer diameter of the post is smaller than the inner diameter of male Luer tip fitting. This provides for a fluid flow in-between the exterior surface of the post and the interior surface of male Luer tip fitting; whereas the flow of air that is drawn into the connector from the inlet, passes via the post into the interior lumen of a receptacle, without intermingling with the concomitantly fluid flow from the receptacle.

7 Claims, 4 Drawing Sheets

(56) References Cited

U.S. PATENT DOCUMENTS

| | | | |
|---|---|---|---|
| 7,497,848 B2 | 3/2009 | Leinsing et al. | |
| 7,658,733 B2 * | 2/2010 | Fangrow | A61J 1/2089 604/403 |
| 7,815,168 B2 * | 10/2010 | Vangsness et al. | 251/149.2 |
| 8,042,690 B2 * | 10/2011 | Lewis | 206/471 |
| 8,480,645 B1 * | 7/2013 | Choudhury | A61M 5/3297 604/405 |
| 2006/0106360 A1 * | 5/2006 | Wong | A61J 1/2096 604/411 |
| 2007/0007478 A1 | 1/2007 | Leinsing et al. | |
| 2008/0287906 A1 * | 11/2008 | Burkholz et al. | 604/500 |
| 2009/0149819 A1 | 6/2009 | Chelak | |
| 2011/0160662 A1 * | 6/2011 | Stout | A61M 25/0097 604/122 |

* cited by examiner

VENTED LUER TIP CONNECTOR

CROSS REFERENCE TO RELATED APPLICATIONS

Technical Field

The present invention generally relates to medical devices. In particular, the invention relates to a vented connector to be used with male Luer fittings.

BACKGROUND OF THE INVENTION

U.S. Pat. Nos. 7,497,848, 7,184,825, 6,706,022 and Patent Applications Ser. Nos. 20090149819, 20070007478 are believed to represent the current state of the art.

SUMMARY OF THE INVENTION

A vented connector, used with male Luer tip fitting, is disclosed. The connector includes axial and bifurcating portions. The axial portion includes an exterior housing and interior post. The lumen of the post forms a continuum with an air inlet. The air inlet is furnished with a filter or membrane element, selectively allowing for the flow of air to pass therethrough while preventing an outflow of fluids therefrom. The outer diameter of the post is smaller than the inner diameter of male Luer tip fitting. This provides for a fluid flow in-between the exterior surface of the post and the interior surface of male Luer tip fitting; whereas the flow of air that is drawn into the connector from the inlet, passes via the post into the interior lumen of a receptacle, without intermingling with the concomitantly fluid flow from the receptacle.

Other features and advantages of the instant invention will become apparent from the following description of the invention which refers to the accompanying drawings.

BRIEF DESCRIPTION OF THE DRAWINGS

The present invention will be understood and appreciated more fully from the following detailed description taken in conjunction with the appended drawings in which.

Figure 1:
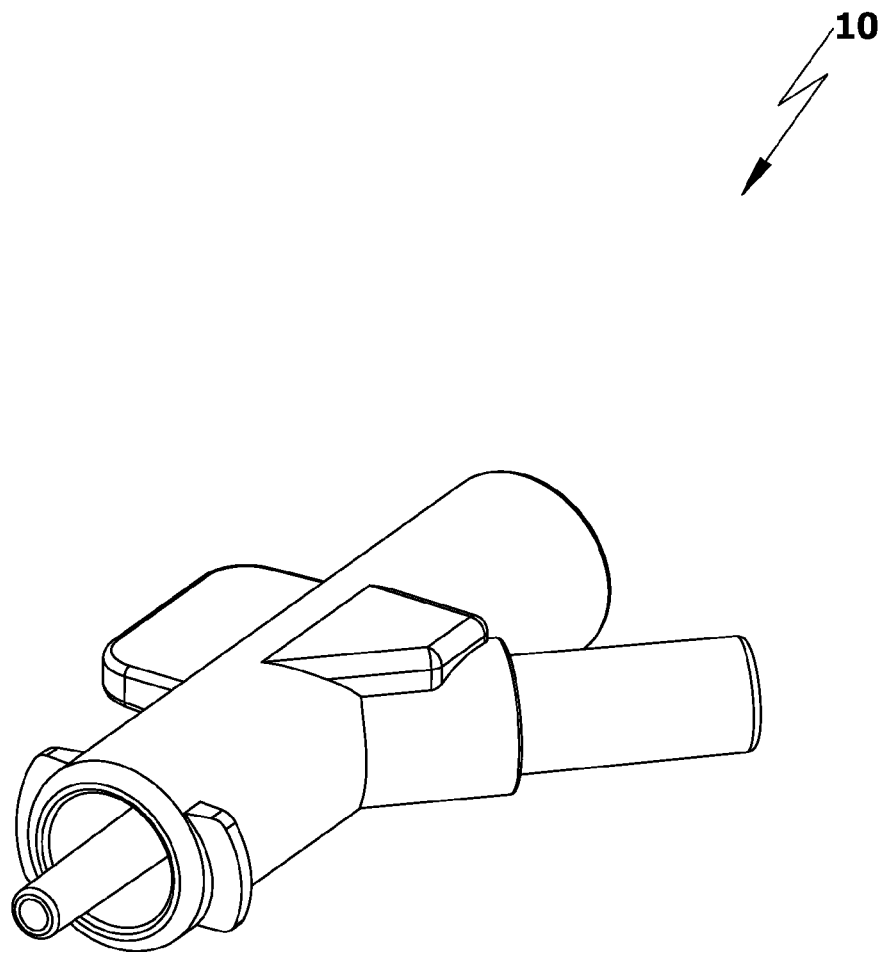
FIG. 1 is an isometric view of the vented connector, in accordance with one aspect of the invention.

While the invention is susceptible to various modifications and alternative forms, specific embodiments thereof have been shown by way of example in the drawings. The components in the drawings are not necessarily to scale, emphasis instead being placed upon clearly illustrating the principles of the present invention.

It should be understood, however, that the description herein of specific embodiments is not intended to limit the invention to the particular forms disclosed, but on the contrary, the intention is to cover all modifications, equivalents, and alternatives falling within the scope of the invention.

DETAILED DESCRIPTION OF THE INVENTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with technology- or business-related constraints, which may vary from one implementation to another. Moreover, it will be appreciated that the effort of such a development might be complex and time-consuming, but would nevertheless be a routine undertaking for those of ordinary skill in the art having the benefit of this disclosure.

Figure 2:
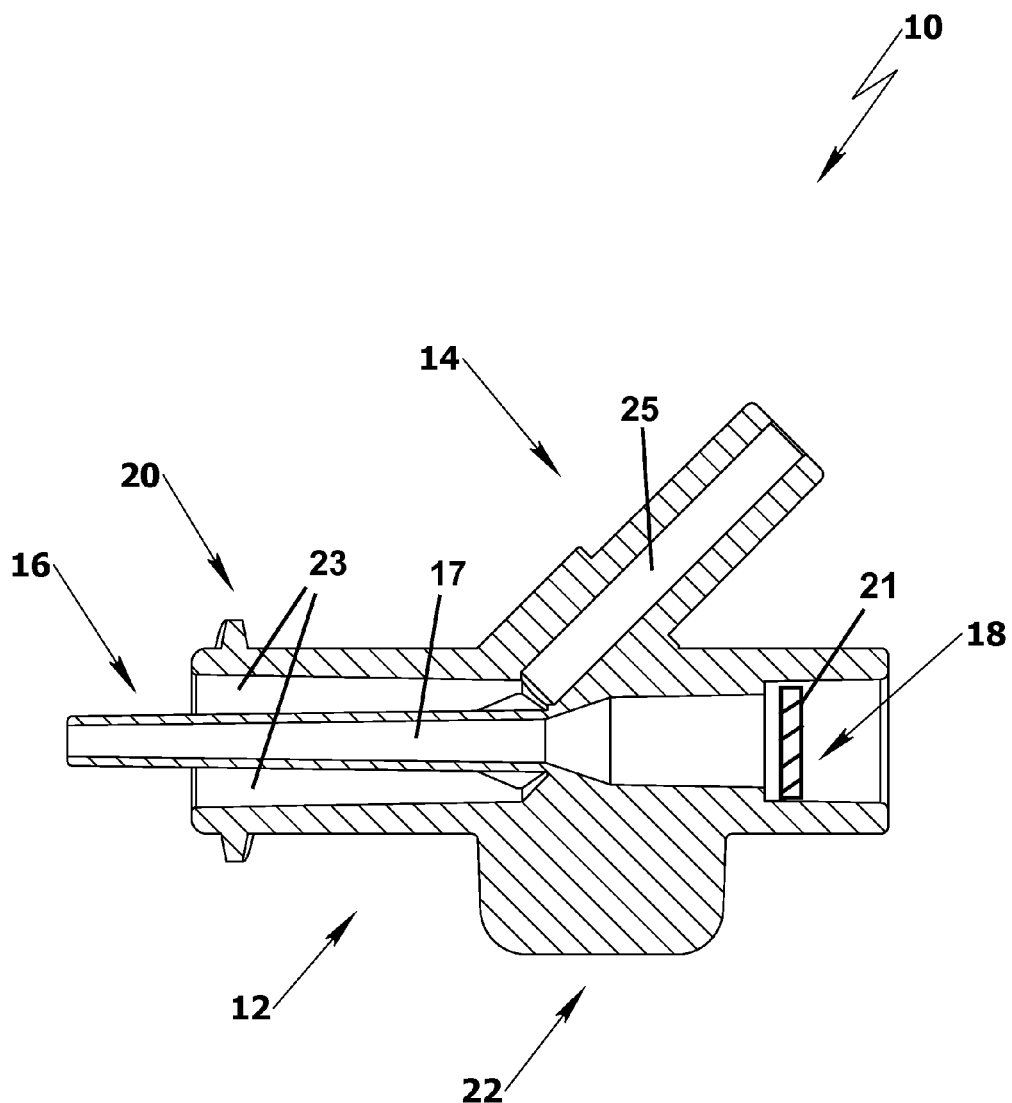
FIG. 2 is a cross-sectional view of the vented connector, in accordance with one aspect of the invention.

FIGS. 1 and 2 show a vented connector 10, in accordance with some embodiments of the present invention. Connector 10 comprises axial portion 12 and bifurcating portion 14. Axial portion 12 comprises interior post portion 16, including an interior post lumen 17 of which forming a continuum with air inlet 18, and exterior housing portion 20. Post 16 is located at the proximal end of connector 10, whereas air inlet 18 is located at the distal end thereof. Exterior housing portion 20 may be furnished with male Luer lock matching protrusions/jags and/or a griping handle, such as lever 22.

Housing portion 20 is adapted to receive a male Luer tip fitting of a receptacle, preferably of a syringe (not shown), so that the exterior surface of the male Luer fitting abuts the interior surface of housing portion 20 in a sealing engagement. Housing portion 20 includes a generally annular-shaped housing portion lumen 23 that forms a continuum with the bifurcating portion lumen 25 of bifurcating portion 14, which serves as the outlet for the fluid outflow from housing portion 20 of connector 10, as will be elaborated infra Bifurcating portion 14 preferably matches standard male/female Luer fittings and may be furnished with the corresponding male/female Luer lock protrusions, jags, grooves or ridges. As seen in FIG. 2, interior post lumen 17 and housing portion lumen 23 are coaxially arranged.

The outer diameter of post 16 is somewhat smaller than the inner diameter of the male Luer tip fitting (not shown) of the receptacle (not shown) inserted into housing 20; thereby providing for a fluid flow in-between exterior surface of post 16 and the interior surface of the male Luer tip fitting. In order to facilitate the co-occurrence of the air flow from inlet 18 throughout post 16 into the interior of the receptacle and the fluid flow from the interior of the receptacle in-between the exterior surface of post 16 and the interior surface of the male Luer tip fitting into the lumen 23 of housing 20, without intermingling with each other, the assembly comprising the receptacle/male Luer tip fitting and connector 10 is to assume an upright position, i.e. so that the distal end of connector 10 faces downwards, while the proximal end of connector 10 faces upwards.

Post 16 preferably extends outboard of the male Luer tip fitting, when the male Luer tip fitting is inserted into post 16 whereby the air that is drawn into connector 10 via inlet 18 passes throughout post 16 into the interior lumen 17 of the receptacle, without intermingling with the concomitantly occurring fluid flow into the lumen 17 of housing 20, in-between the exterior surface of post 16 and the interior surface of the male Luer tip fitting. Post 16 preferably extends past the male Luer tip fitting, so that the entrance point of the air drawn into the receptacle, namely the proximal end of post 16, is located above the outlet at the base of male Luer tip fitting, namely where the fluid is drawn from the receptacle in-between the exterior surface of post 16 and the interior surface of the male Luer tip fitting. In accordance with some preferred embodiments of the connector of the present invention, the tolerance of the gap between the proximal end of post 16 and the aforementioned outlet at the base of male Luer tip fitting, namely where the fluid is drawn from the receptacle, is more than about 2 mm but less than about 6 mm.

Inlet 18 is preferably furnished with a specific filter or membrane element 21 configured to selectively allow for the flow of air to pass therethrough into the lumen 17 of post 16, while preventing an outflow of fluids therethrough, from the lumen 17 of post 16 out of Inlet 18. The selective filter or membrane element 21 is configured to allow the flow of air therethrough while being wet, soaked, drenched or otherwise saturated with the fluid, which may gutter thereto from the receptacle due to the gravitational force. The selective filter or membrane element 21 is preferably configured to facilitate delivery of sterile air/gas into connector 10. An example of a filter or membrane element 21 thus configured is the VERSAPOR® R membrane—FluoRepel™ Treated membrane, available from Pall Corp corporation, 2200 Northern Boulevard East Hills, N.Y. 11548-1289, Cat. Nos. 6694197, 6704192 and 6304185.

Bifurcating portion 14, which serves as the outlet for the fluid outflow from housing 20 of connector 10, can be furnished with a specific filter or membrane element of the second type, functioning in essentially opposite manner to the filter or membrane element of the first type. The specific filter or membrane element of the second type is permeable for fluids, selectively allows for the outflow of fluids to pass therethrough, into a tubing set that may be connected thereto, while retaining the air and preventing an outflow thereof from connector 10; thereby precluding the formation of air emboli in the fluid drained from connector 10.

Figure 3:
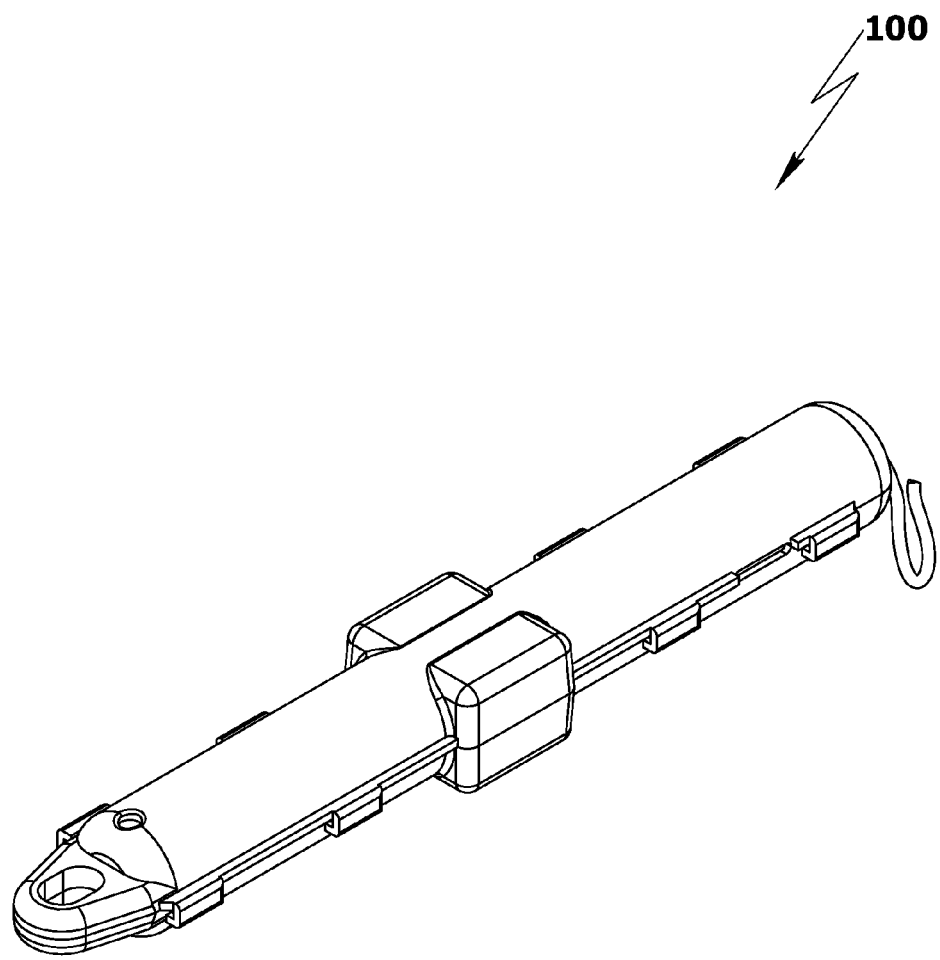
FIG. 3 is an isometric view of the casing, preferably to be used with the vented connector, in accordance with another aspect of the invention.
Figure 4:
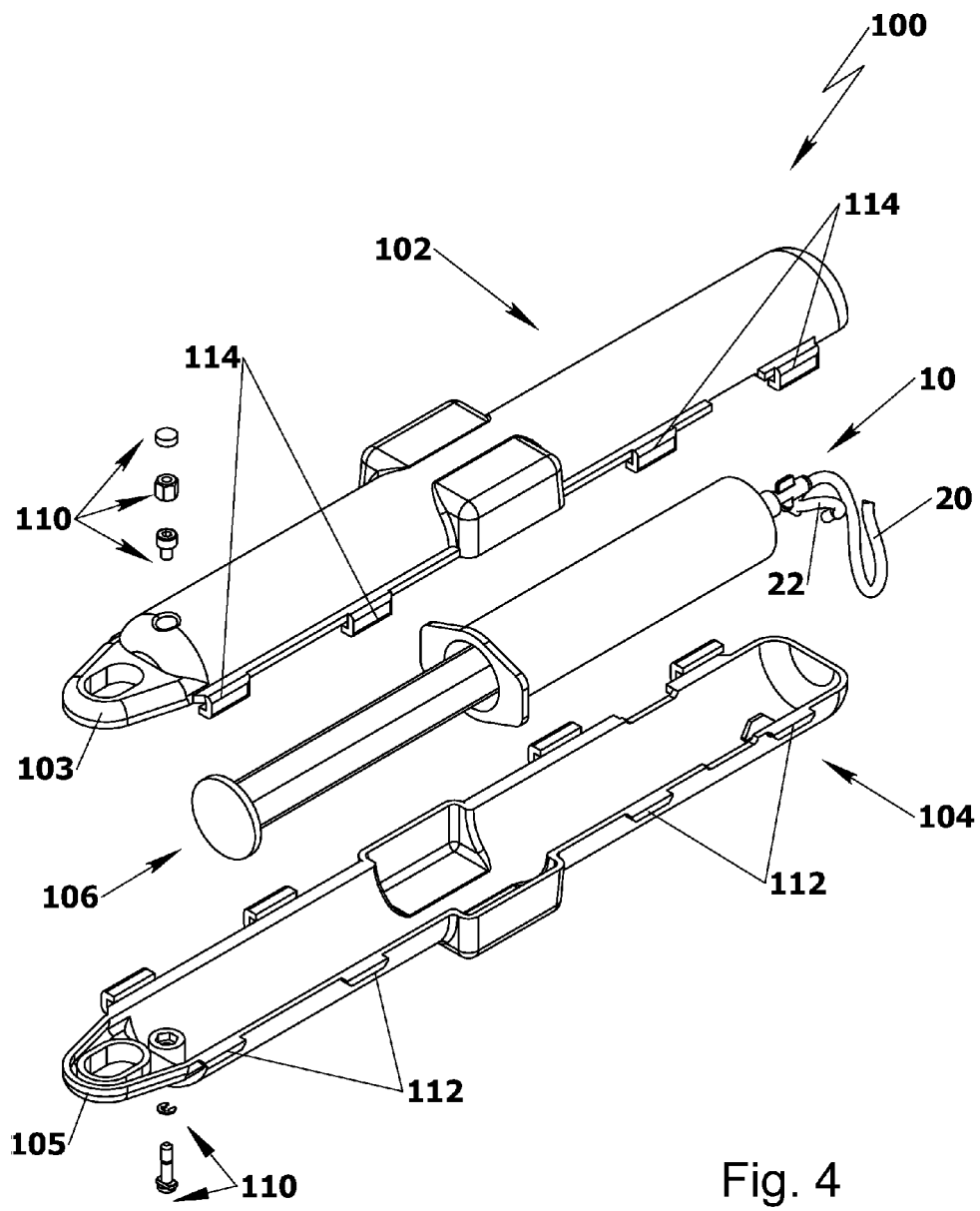
FIG. 4 is an exploded isometric view of the casing, preferably to be used with the vented connector, in accordance with another aspect of the invention.

It is further disclosed that in accordance with another aspect of the present invention, in order to achieve the upright positioning of the aforementioned assembly comprising the receptacle/male Luer tip fitting and vented connector 10, shown in FIGS. 1 and 2, i.e. so that the distal end of connector 10 faces downwards while the proximal end faces upwards, connector 10 is preferably incorporated within the assembly setup of system 100, shown in FIGS. 3 and 4, to which reference is now made. System 100 comprises subunits 102 and 104 forming the casing, having eyelet tab portions 103 and 105 respectively. Casing subunits 102 and 104 are adapted to accommodate receptacle 106, preferably a syringe of a standard type. Subunits 102 and 104 may be secured in an assembled state by the means of bolt subassembly 110, which in a non-limiting manner may include bolts, nuts, washers, split or spring washers or rings, and a cork element. Additionally or alternatively, to secure the casing in the assembled state, subunits 104 and 102 can be furnished with slidably interlocking elements 112 and 114 respectively.

Connector 10 is preferably provided within a sterilized packaging (not shown). Connector 10 is mounted onto the male Luer tip fitting of syringe receptacle 106. System 100 is preferably employed with infusion sets, pumps, connectors or manifolds and used to administrate the content of the receptacle, or particularly of a syringe receptacle, into the patient or into the a perfusion tubing system, exemplified by conduits 20, which may be connected to the air inlet of connector 10, and 22, which is typically connected to the fluid outlet, i.e. the bifurcating portion of connector 10. System 100 is typically hanged in an upright position from the eyelet tab and provides for administrating the content of a rigid-shell receptacle, such as syringe 106, by maintaining an inflow of air thereto, as elaborated supra. The rigid-shell receptacle, such as syringe 106, may contain any medical fluid, inter alia, including saline or other physiological aqueous solutions, liquid or dissolved drugs or medications, etc.

It will be appreciated by persons skilled in the art that the present invention is not limited by what has been particularly shown and described herein above. Rather the scope of the invention is defined by the claims which follow:

What is claimed is:

1. A system for administration of a medical fluid comprising:
    a receptacle, having at least one of its outlets/inlets furnished with a male Luer tip fitting having a base;
    a vented connector, attached to the base of said male Luer tip fitting,
    wherein said connector comprises an axial portion and a bifurcating portion; said axial portion comprising an interior post and an exterior housing, said post forming a continuum with an air inlet, wherein said air inlet is in fluid communication with the interior post and said air inlet comprises a filter or membrane element configured to selectively allow the flow of air to pass therethrough while preventing an outflow of fluids therefrom, and said axial portion comprises coaxially arranged lumens in the form of an interior lumen through which said flow of air passes into said receptacle; and an exterior lumen through which fluid from said receptacle passes to said bifurcating portion; and
    a casing for said receptacle, comprising two complementary subunits having eyelet tab portions that are configured and disposed so that said casing, encompassing said receptacle, can be hung from said eyelet tab portions to attain an upright position, whereby a continuous administration of the content of said receptacle can be achieved by maintaining an inflow of air to the receptacle.

2. The system as in claim 1, wherein said connector is characterized by that the proximal end of said post surpasses the outlet at the base of said male Luer tip fitting.

3. The system as in claim 1, wherein said receptacle is a rigid-shell receptacle.

4. The system as in claim 1, wherein said receptacle is a syringe of a standard type, having male Luer tip fitting.

5. The system as in claim 1, wherein said complementary subunits of the casing are furnished with slidably interlocking elements.

6. The system as in claim 1, wherein said complementary subunits of the casing are secured in an assembled state by bolt subassembly, comprising one or more of: a bolt, nut, washer, split or spring washer or ring and a cork element.

7. The system as in claim 6, wherein said housing matches standard male/female Luer fittings.

\* \* \* \* \*